United States Patent [19]

Appelgren et al.

[11] Patent Number: 4,888,179

[45] Date of Patent: Dec. 19, 1989

[54] DIURETIC COMPOSITION

[75] Inventors: Curt H. Appelgren, Kungsbacka; Eva C. Eskilsson, Mölnlycke, both of Sweden

[73] Assignee: Lejus Medical Aktiebolag, Mölndal, Sweden

[21] Appl. No.: 144,229

[22] Filed: Jan. 15, 1988

[30] Foreign Application Priority Data

Jan. 15, 1987 [SE] Sweden .................................. 8700137

[51] Int. Cl.⁴ .............................................. A61K 9/36
[52] U.S. Cl. .................................... 424/480; 424/482
[58] Field of Search ............... 424/490, 494, 495, 496, 424/497, 480, 482

[56] References Cited

U.S. PATENT DOCUMENTS 4,716,041 12/1987 Kjornaes et al. .................... 424/468
4,728,512 3/1988 Mehta et al. ......................... 424/458

Primary Examiner—Thurman K. Page
Attorney, Agent, or Firm—Millen, White & Zelano

[57] ABSTRACT

The present invention relates to a multiple-unit dose composition comprising furosemide as pharmaceutically active compound, whereby the composition gives a release of furosemide in accordance with Dissotest in a buffer having pH 1.5 of at most 4% during hour 1, a release in a buffer having pH 5.5 of at most 7.5% during a consecutive hour (hour 2), a release of furosemide in a buffer having pH 7.5 of at least 65% during a further consecutive hour (hour 3), and a release of furosemide in a buffer having pH 7.5 of at least 90% during a consecutive hour (hour 4).

15 Claims, 1 Drawing Sheet

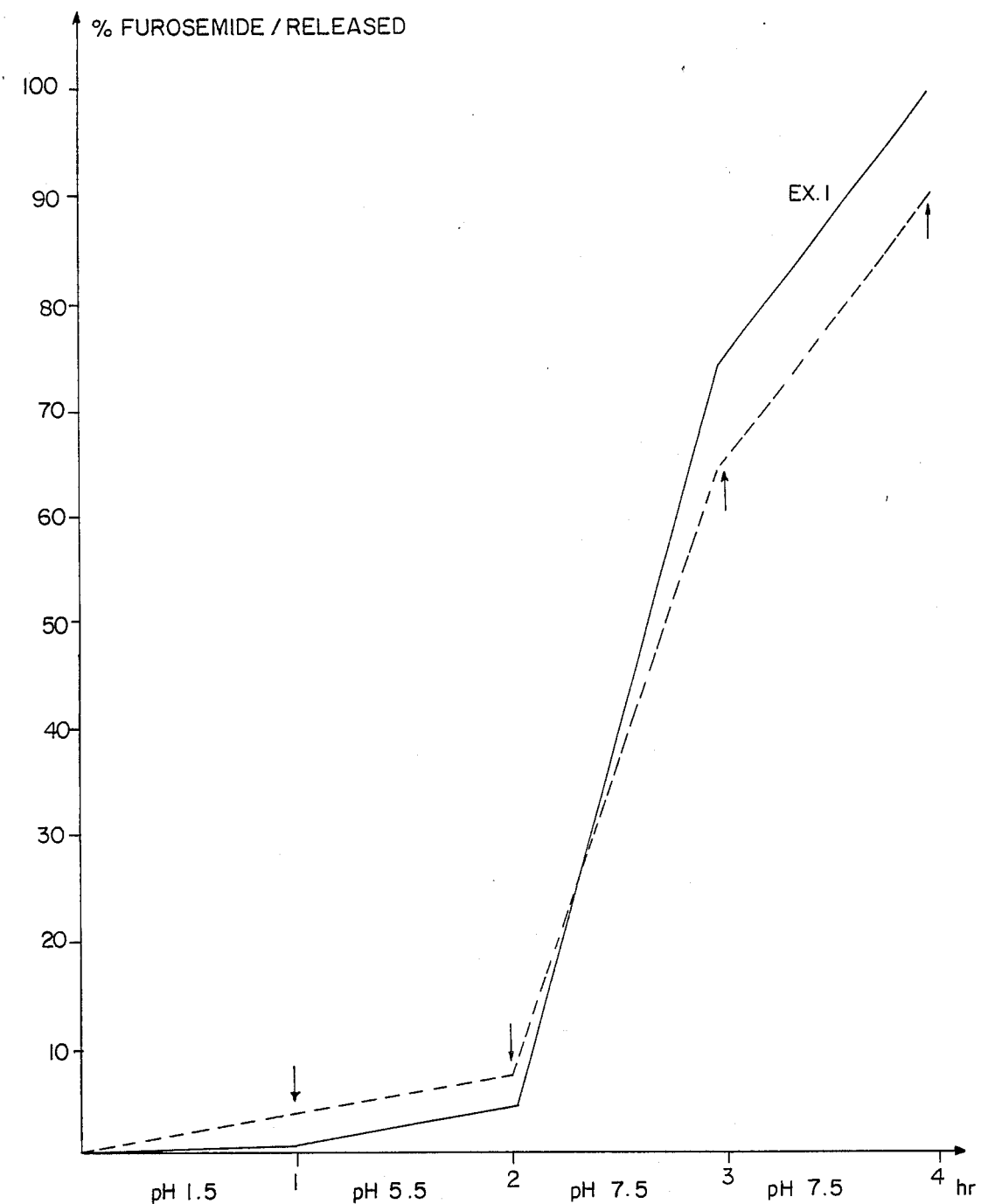

DIURETIC COMPOSITION

TECHNICAL FIELD

The present invention relates to a diuretic composition in multiple-unit dosage form which comprises furosemide, as the active ingredient.

An object of the present invention is to provide a diuretic composition which when used minimizes the fluctuations of the plasma values. Another object of the invention is to provide a diuretic which minimizes the side effects of high plasma peak concentrations.

BACKGROUND OF THE INVENTION

It is previously known from U.S. Pat. No. 4,324,779 that a diuretic composition of furosemide, shows an increased solubility, and absorption in the body at a pH of about 4. This means that this composition dissolves in the stomach, or dissolves and is absorbed very early in the upper part of the intestinal tract, which leads to very high plasma peaks. As pH varies in the stomach, the release rate of furosemide will vary considerably. This results in a varying load on the body, which is unsuitable from a therapeutic point of view.

Furosemide is preferably used in the long term treatment of cardial oedema, or oedema of a light to medium severe degree, as well as in the treatment of light to medium severe hypertonia, particularly when there is diminished kidney function, or diabetes. Furosemide is also used in case of congestive heart failure.

It is desirable to have a diuretic composition with a more even release profile.

DESCRIPTION OF THE PRESENT INVENTION

According to the present invention a composition is provided which meets the above requirements characterized in that the composition has a release rate in an aqueous medium having a pH of 1.5 of less than 4%, preferably less than 2%, of furosemide after 1 hr (hour 1), a release rate in an aqueous medium having a pH of 5.5 of less than or equal to 7.5% of furosemide during the second hour (hour 2), a release rate in an aqueous medium having a pH of 7.5 of at least 65% during a third hour (hour 3), and a release rate in the same medium having a pH of 7.5 of at least 90% of furosemide during the fourth hour (hour 4).

BRIEF DESCRIPTION OF THE DRAWING

The sole FIGURE illustrates the release profile of Example 1.

According to the present invention, substantially no release of the active compound takes place in the stomach. Instead, the stomach functions as a depot of a multiple-unit dosage and it can by degrees continously release the composition in the form of pellets, having diameters of from about 0.5–1.5 mm, into the intestine. These pellets are dissolved and release furosemide at the desired rate in the higher pH ranges existing therein.

According to the invention the pH variations of the stomach, pH 1–5, are prevented from having an effect on the release rate, which will otherwise take place in the stomach due to the low $pk_a$ of the furosemide, $pk_a=3.9$.

According to U.S. Pat. No. 4,324,779 it has not been possible to obtain a release rate below 10% at a pH of 5.5 during the second hour of release. This is the reason why such large fluctuations have been obtained using such compositions. As a substantial release in pH 5.5 by such a type of compositions causes that a still higher release rate is obtained in a pH around 4.

The above described release rates of the compositions according to the present invention have been measured in a Dissotest (Sotax AG), with a flow of 100 ml/hr, whereby the aqueous medium having a pH of 1.6 is a buffer solution of a mixture of 33.8 parts by volume of an aqueous solution containing 7.507 g of amino acetic acid, 5.84 g of sodium chloride per liter, and 66.2 parts by volume of 0.1N hydrochloric acid. The mixture contains 0.01% polyoxyethylene sorbitan oleate.

The aqueous medium having a pH 5.5 consists of a mixture of 3.9 parts of a 1/15M disodium hydrogenphosphate solution, and 96.1 parts of a 1/15M potassium dihydrogenphosphate solution, to which total mixture 0.01% polyoxyethylene sorbitan oleate has been added.

The aqueous medium having a pH of 7.5 consists of 6.805 g of potassium dihydrogenphosphate, and 1.630 g of sodium hydroxide per liter.

The release rate is determined at 37° C. and atmospheric pressure.

In a further test using an aqueous medium having a pH of 4.6 solely, the release rate of furosemide was less than 2% after one hour, and less than 4% after two hours in said medium when tested according to USP XXI <711> apparatus 2, 100 rpm. The aqueous medium consisted of an acetate buffer having the composition 30.69 g of acetic acid (99.8%), and 40.19 g of sodium acetate dissolved in destilled water to 10 liters. The present composition according to Example 1 below shows an extremely low release rate of furosemide even at a pH above the $pk_a$ of the furosemide. The test in pH 4.6 was carried out without any pre-exposure in the pH 1.5 range.

The particle size of the tested products was 0.5 to 1.5 mm.

The invention will be described in greater detail with reference to the examples given below, however, without being restricted thereto.

EXAMPLE 1

A core comprising 30% furosemide, N-(2-furfuryl)-4-chloro-5-sulfamoyl-antranilic acid, was prepared as follows. Microcrystalline cellulose, 4%, furosemide, and lactose, or mannitol and lactose, 40%, and starch, 20%, were mixed dry.

To this dry mixture was added a buffer solution of potassium dihydrogenphosphate and sodium hydroxide having a pH of 6.8 to form a moist powder mass. The buffer solution is the granulation liquid, which has a capacity to solve some of the furosemide. The resultant mixture provides a suitable binder for the mass. About 5% of the ingoing furosemide is dissolved in the buffer solution. The resultant powder mass is extruded in an extruder (NICASYSTEM), whereupon the extrudate is spheronized in a spheronizer (NICASYSTEM). These spherical granules having a diameter of about 0.5–1.5 mm, were then coated with an inner layer of ethyl cellulose, about 2%, and hydroxypropylmethyl cellulose, (Pharmacoat), about 2%, (40:60–60:40), and an outer layer consisting of hydroxypropyl methyl cellulose phthalate, $pk_a$ 5.5, in an amount of 1–10% by weight, preferably 2–6% by weight.

The inner layer of ethyl cellulose and hydroxypropyl methyl cellulose can be 1.5–10% by weight. The hydroxypropyl methyl cellulose can be exchanged with hydroxypropyl cellulose, (Klucel), polyethylene glycol, (PEG), or a water soluble polyvinyl pyrrolidone in suitable amounts.

The hydroxypropyl methyl cellulose phtalate (HP 55) can be completely or partly exchanged with other anionic polymers as well, such as cellulose acetate phtalate, (CAP), or EUDRAGITE® L or EUDRAGITE® S types, which are copolymers.

The core above can contain 20 to 80% of furosemide, whereby 30 to 40% by weight are preferred.

The coating of the cores can either take place in a fluid bed or using a conventional pan coating, or using a so called Kugelcoater.

The coated core according to Example 1 above was tested in a Dissotest using the above described buffer solutions as the release media. The result of this release test is shown in attached FIG. 1, which illustrates the release curve, as well as the release profile described with respect to example 1, above.

EUDRAGITE L and S are copolymers of methacrylic acid and methacrylic acid methylester containing free acid groups, whereby the acid to ester ratio in the L-type is 1:1, and the acid to ester ratio in the S-type is 1:2.

We claim:

1. A multiple-unit dose composition comprising furosemide, N-(2-furfuryl)-4-chloro-5-sulfamoyl-antranilic acid, as pharmaceutically active compound, characterized in that the composition in a release test using Dissotest, 100 ml/hr, in an aqueous medium having pH 1.5 gives a release of furosemide of less than 4% during 1 hr, and in the same test in an aqueous medium having pH 5.5 gives a release of furosemide of less than or equal to 7.5% during a following hour, (hour 2), and in the same test, in an aqueous medium having pH 7.5 gives a release of furosemide of at least 65% during a further following hour, (hour 3), and in the same test in the same aqueous medium having pH 7.5 gives a release of furosemide of at least 90% during a further following hour, (hour 4).

2. Composition according to claim 1, characterized in that the release in an aqueous medium having pH 1.5 is at most 2% during one hour.

3. Composition according to claim 1, characterized in that it comprises a core having a content of furosemide of 20 to 80% by weight, coated with a laminate having an inner layer of ethyl cellulose and hydroxypropyl methyl cellulose in an amount of at least 1.5% by weight, and an outer layer of hydroxypropyl methyl cellulose phtalate having $pk_a = 5.5$ in an amount of at least 1% by weight.

4. A multiple-unit dose composition comprising a core, an inner coating and an outer coating, said core comprising about 4% microcrystalline cellulose, about 20% starch, about 30% furosemide, and about 10% lactose, said inner coating comprising ethyl cellulose, said composition having a release rate for furosemide of less than 4% in an aqueous medium with a pH of 5.5 during a first hour, a release rate for furosemide equal to or less than 7.5% in an aqueous medium with a pH of 5.5 during a second hour, a release rate of furosemide of at least 65% in an aqueous medium with a pH of 7.5% during a third hour, and a release rate of furosemide of at least 90% in the same aqueous medium having a pH of 7.5 during a fourth hour.

5. Composition according to claim 4, characterized in that the inner layer consists of ethyl cellulose and hydroxypropyl cellulose.

6. Composition according to claim 4, characterized in that the inner layer consists of ethyl cellulose and polyethylene glycol.

7. Composition according to claim 4, characterized in that the inner layer consists of ethyl cellulose and water soluble polyvinyl pyrrolidone.

8. Composition according to claim 4, characterized in that the outer layer consists of cellulose acetate phtalate.

9. Composition according to claim 4, characterized in that the outer layer consists of a copolymer of methacrylic acid and methacrylic acid methyl ester containing free acid groups wherein the acid to ester ratio is 1:1 and a similar copolymer wherein the acid to ester ratio is 1:2.

10. Composition according to claim 4, characterized in that the inner layer comprises up to 10% by weight.

11. Composition according to claim 4, characterized in that the outer layer comprises up to 10% by weight.

12. A multiple-unit dose composition comprising a core, an inner coating, and an outer coating, said core comprising about 4% microcrystalline cellulose, about 20% starch, about 30% furosemide, and about 10% lactose, said inner coating comprising about 2% ethyl cellulose and about 2% hydroxypropylmethyl cellulose in a 40:60–60:40 ratio, said outer coating comprising about 1–10% hydroxypropylmethyl cellulose phthalate having a $pk_a$ of 5.5, said composition having a release rate of furosemide of less than 4% during a first hour in an aqueous medium with a pH of 1.5, a release rate of furosemide equal to or less than 7.5% in an aqueous medium with a pH of 5.5 during a second hour, a release rate of furosemide of at least 65% in an aqueous medium with a pH of 7.5 during a third hour, and a release rate of furosemide of at least 90% in the same aqueous medium having a pH of 7.5 during a fourth hour.

13. A composition according to claim 4, characterized in that the outer layer consists of a copolymer of methacrylic acid and methacrylic acid methyl ester containing free acid groups wherein the acid to ester ratio is 1:1, and another copolymer of methacrylic acid and methacrylic acid methyl ester containing free acid groups wherein the acid to ester ratio is 1:2.

14. A composition according to claim 4, characterized in that the outer layer consists of a copolymer of methacrylic acid and methacrylic acid methyl ester containing free acid groups wherein the acid to ester ratio is 1:1.

15. A composition according to claim 4, characterized in that the outer layer consists of a copolymer of methacrylic acid and methacrylic acid methyl ester wherein the acid to ester ratio is 1:2.

* * * * *